(12) United States Patent
Robinson et al.

(10) Patent No.: US 11,358,929 B1
(45) Date of Patent: *Jun. 14, 2022

(54) BIOBASED DIISOCYANATES, AND PROCESS FOR PREPARATION OF SAME

(71) Applicant: Evoco Limited, Toronto (CA)

(72) Inventors: Jason James Robinson, Toronto (CA); Juri Helmut Moebus, North York (CA); Tristan Calayan, Mississauga (CA); Guerino G. Sacripante, Oakville (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/540,462

(22) Filed: Dec. 2, 2021

Related U.S. Application Data

(63) Continuation of application No. 17/245,807, filed on Apr. 30, 2021.

(51) Int. Cl.
*C07C 263/10* (2006.01)
*C08G 18/42* (2006.01)
*C08G 18/76* (2006.01)

(52) U.S. Cl.
CPC ............ *C07C 263/10* (2013.01); *C08G 18/42* (2013.01); *C08G 18/7614* (2013.01); *C08G 18/7657* (2013.01)

(58) Field of Classification Search
CPC ....................................................... C07C 263/10
See application file for complete search history.

(56) References Cited

U.S. PATENT DOCUMENTS 4,597,910 A * 7/1986 Konig ................. C08G 18/771
528/48

4,820,866 A * 4/1989 Sanders ................ C07C 265/12
560/358

(Continued)

OTHER PUBLICATIONS

Ghatge 1. Syntheses of Diisocyanates Based on Cashewnut Shell Liquid. Indian Journal of Technology, vol. 17, Feb. 1979, pp. 55-57). (Year: 1979).*

(Continued)

*Primary Examiner* — Michael M Dollinger

(57) ABSTRACT

Biobased diisocyanates are derived from 3-petadecyl phenol, which is derived from Cardanol harvested from cashew nutshell liquid food waste. The biobased diisocyanates are of the formulas:

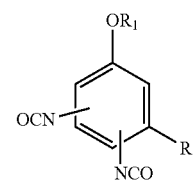

1

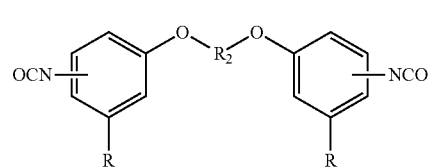

2 wherein R is an alkyl chain $C_{15}H_{31}$ (n-pentadecyl); $R_1$=$CH_3$ or $COCH_3$; and $R_2$ is an alkylene of from about 1 to 18 carbon atoms.

15 Claims, 5 Drawing Sheets

1

2 where:

R is an alkyl chain $C_{15}H_{31}$ (n-pentadecyl)

$R_1$ = $CH_3$ or $COCH_3$;

$R_2$ is an alkylene of from 1 to 18 carbon atoms.

(56) References Cited

U.S. PATENT DOCUMENTS

| | | | | |
|---|---|---|---|---|
| 4,870,206 | A | * | 9/1989 | Sanders ................ C07C 265/12 |
| | | | | 528/85 |
| 4,888,125 | A | * | 12/1989 | Konig ................... C07C 265/12 |
| | | | | 560/339 |
| 5,731,399 | A | * | 3/1998 | Carter ................... C07C 265/12 |
| | | | | 528/68 |
| 6,329,344 | B1 | * | 12/2001 | Arora ..................... C07H 13/12 |
| | | | | 514/6.9 |
| 11,214,539 | B1 | * | 1/2022 | Robinson ........... C08G 18/7678 |
| 2014/0018530 | A1 | * | 1/2014 | Tanaka ............... C08G 18/8067 |
| | | | | 536/69 |
| 2014/0024824 | A1 | * | 1/2014 | Tanaka ................... C08B 15/06 |
| | | | | 536/58 |
| 2017/0369427 | A1 | * | 12/2017 | Wadgaonkar ......... C07C 263/12 |

OTHER PUBLICATIONS

Ghatge 2. Studies on the Reactivities of Diisocyanates. Die Angewandte Makromolekulure Chemie 19 (1971) 75-81 (Nr. 249) (Year: 1971).*

* cited by examiner where:

R is an alkyl chain $C_{15}H_{31}$ (n-pentadecyl)

$R_1$ = $CH_3$ or $COCH_3$;

$R_2$ is an alkylene of from 1 to 18 carbon atoms.

where:

R is an alkyl chain $C_{15}H_{31}$ (n-pentadecyl)

$R_1$ is an alkyl group of from 1 to 18 carbon atoms where:

R is an alkyl chain $C_{15}H_{31}$ (n-pentadecyl)

$R_2$ is an alkylene moiety from 1 to 18 carbon atoms where:

R is an alkyl chain $C_{15}H_{31}$ (n-pentadecyl)

$R_1$ = $CH_3$ or an acetyl group ($COCH_3$)

where:

R is an alkyl chain $C_{15}H_{31}$ (n-pentadecyl)

$R_2$ is an alkylene of from 1 to 18 carbon atoms

BIOBASED DIISOCYANATES, AND PROCESS FOR PREPARATION OF SAME

CROSS-REFERENCE TO RELATED APPLICATION

This application is a continuation of U.S. patent application Ser. No. 17/245,807 filed on Apr. 30, 2021, the content of which is incorporated herein by reference in its entirety.

FIELD

This disclosure is generally directed to diisocyanates, and in particular to organic diisocyanates that are bio-derived from natural sources or derived from biomass starting materials such as Cardanol or Hydrogenated Cardanol also known as 3-pentadecylphenol. Specifically, this disclosure further provides biobased diisocyanates of the structures 1 and 2 shown in FIG. 1, and to methods for their preparation.

BACKGROUND

Polyurethanes are a large class of polymers used in a wide range of applications, such as construction, automotive, furniture, footwear, insulation, coatings, adhesives, elastomer foams, and consumer goods. Polyurethanes are produced from the polymerization reaction between polyols and/or aliphatic diols with diisocyanates. Usually, the polyols are hydroxyl-terminated oligomers or polymers, such as poly (ethylene oxide), poly (propylene oxide), poly (alkylene glycols) or polyester resin with terminal hydroxyl groups. The diisocyanates are usually selected as toluene-diisocyanate, 4,4'-methylene diphenyl diisocyanate, isophorone diisocyanate and hexamethylene diisocyanate. The properties of polyurethanes vary depending on the structure of the polymer backbone and can be tailored to have high strength and rigidity, or high flexibility and toughness. When a polyol (and or aliphatic diol) reacts with the diisocyanate, it forms a linear, thermoplastic polymer. If crosslinking agents are utilized, such as diethanol amine, polyhydric alcohol or polyols with three or more hydroxyl moieties and/or poly-isocyanates with 3 reactive isocyanate groups, varying degree of crosslinking in the polyurethane product can be tailored to achieve a rigid, cross-linked, thermosetting polyurethane. Additionally, additives are commonly added during the reaction of the polyurethane to improve certain properties, such as chain-extending agents, blowing agents, surfactants, fillers, plasticizers, pigments and flame retardants. Blowing agents will create a polyurethane foam, and surfactants will control the bubble formation and, therefore, the cell formation of the foam. In general, fillers increase stiffness, plasticizers reduce hardness and pigments add colour to the material. Additionally, there are many aromatic and aliphatic poly-isocyanates; however, the most important of these, are toluene diisocyanate (TDI) and 4,4'-methylene diphenyl diisocyanate (MDI), which are used in the production of around 95% of all polyurethanes. TDI is generally used in the production of soft, flexible foams for cushioning, whereas MDI is used in the production of more versatile, rigid polyurethanes. Other less common diisocyanates such as the aliphatic hexamethylene diisocyanate or cycloaliphatic isophorone diisocyanates are known and utilized for polyurethane compositions useful in specialty applications, such as enamel paints and coatings which are resistant to abrasion or degradation by ultraviolet light. The main components of the polyurethane, namely the polyols and the diisocyanates, are mainly derived from petrochemicals, and their production contributes heavily towards greenhouse gasses that negatively impact the environment. There is an overall need for polyols and diisocyanates that are based on renewable resource materials derived primarily from a biomass such that there is less dependency on fossil fuels, which accelerate climate change.

Examples of polyols derived from biobased chemicals are known. For example, U.S. Pat. No. 10,934,384 describes selection of biobased polyester-polyols used for producing polyurethane resins. The polyurethanes are obtained from biobased polyols, additives and petrochemically derived diisocyanate such as MDI, to result with an overall biobased content of from about 70 to about 85% by weight of the corresponding polyurethane composition.

U.S. Pat. No. 9,950,996 describes biobased aromatic diisocyanates, wherein the starting materials are namely, bis(4-isocyanato-2-methoxyphenoxy)alkane and bis(4-isocyanato-2, 6-dimethoxyphenoxy) alkanes and are synthesized from vanillic acid/syringic acid which have their origin in bio-resources such Lignin. The aromatic biobased diisocyanates are analogous in structure to oil-derived MDI.

U.S. Pat. Nos. 8,044,166, 9,404,132 and 9,765,369 describe a process for making 1,5-pentylene diisocyanate from bioderived 1,5-pentane diamine obtained from enzymatic decarboxylation of L-lysine. The aliphatic biobased diisocyanates are analogous in structure to oil-derived hexamethylene diisocyanates.

Cawse et al., "Polymers from renewable sources", Die Makromolekulare Chemie, 185 (4) p. 697 (1984), describes the synthesis of furan diisocyanates d from methyl furoate and furfuryl-amine which are bioderived from maize, oats and husks. The aromatic biobased diisocyanates are analogous in structure to MDI, and furthermore are obtained from a food-based bioresource.

There is a need to provide polyurethane compositions wherein the biobased content, for example, is from about 95% to about 100% by weight of the polyurethane composition. While the objective is to increase the renewable content of the polyurethane foam, it is also desirable to maintain or improve the performance properties of the polyurethane composition. To achieve high renewable contents of the polyurethane foam, there is a need for biobased polyols, biobased additives, biobased fillers, biobased colorants and biobased diisocyanates.

There is also a need for biobased diisocyanates that are aromatic and analogous in structure to TDI and MDI. Furthermore, there is a need for biobased diisocyanates that are primarily derived from non-food-based biomass or food-waste biomass.

Furthermore, there is a need to provide biobased aromatic diisocyanates derived form food-waste or non-food biomass, with biobased polyols, fillers, additives and colorants for the production of polyurethane composition for many applications, wherein the bio-content is from about 95% to about 100% by weight of the polyurethane composition.

These and other needs can be achievable with the biobased diisocyanates of the present disclosure.

SUMMARY

Illustrated herein is a biobased diisocyanate that is bio-derived from natural sources or derived from biomass starting materials such as Cardanol or Hydrogenated Cardanol (also known as 3-pentadecylphenol). Cardanol is a phenolic material obtained from cashew nutshell as a food-waste by-product of cashew nut processing. Cardanol and derivatives are raw materials with wide applications in the form of surface coatings, paints and varnishes, and are inexpensive with over 1-million-ton production in 2021. The present invention provides biobased diisocyanates as illustrated in FIG. 1, and wherein structure 1, is an aromatic diisocyanate which is analogous in structure to TDI; and wherein structure 2, is bis-aromatic diisocyanate which is analogous in structure to MDI. The biobased diisocyanates are primarily derived from non-food-based biomass or food-waste biomass, and are from about 70 to about 100% biobased by weight.

Accordingly, in one aspect there is provided a biobased diisocyanate of the formula 1 or 2, as illustrated in FIG. 1, wherein R is an alkyl chain $C_{15}H_{31}$ (n-pentadecyl); $R_1=CH_3$ or $COCH_3$; and $R_2$ is an alkylene of from about 1 to 18 carbon atoms.

The biobased diisocyanate of formula 1 may be selected from the group consisting of: 1,5-diisocyanato-2-methoxy-4-pentadecylbenzene, 1,3-diisocyanato-2-methoxy-4-pentadecylbenzene, 2,4-diisocyanato-5-pentadecylphenyl acetate, and 2,6-diisocyanato-3-pentadecylphenyl acetate, and mixtures thereof.

The biobased diisocyanate of formula 2 may be selected from the group consisting of: 1,2-bis(4-isocyanato-3-pentadecylphenoxy) ethane, 1,2-bis(2-isocyanato-5-pentadecylphenoxy) alkane, 1,2-bis(2-isocyanato-3-pentadecylphenoxy) alkane, 1-isocyanato-2-(2-(4-isocyanato-3-pentadecylphenoxy) alkoxy)-4-pentadecylbenzene, 2-isocyanato-1-(2-(4-isocyanato-3-pentadecylphenoxy) alkoxy)-3-pentadecylbenzene, 2-isocyanato-1-(2-(2-isocyanato-5-pentadecylphenoxy) alkoxy)-3-pentadecylbenzene, and mixtures thereof.

A process for the preparation of the biobased diisocyanate of formula 1, may comprise the steps of: (i) nitration of 3-n-pentadecylphenol to di-nitro-pentadecyl-phenol; (ii) methylation of di-nitro-pentadecyl-phenol to di-nitro-methoxy-pentadecylbenzene; (iii) reduction of di-nitro-methoxy-pentadecylbenzene to di-amino-methoxy-pentadecylbenzene; and (iv) phosgenation of di-amino-methoxy-pentadecylbenzene to diisocyanato-methoxy-pentadecylbenzene.

A process for the preparation of the biobased diisocyanate of formula 1, may comprise the steps of: (i) methylation of 3-n-pentadecylphenol to methoxy-pentadecylbenzene; (ii) nitration of methoxy-pentadecylbenzene to di-nitro-methoxy-pentadecylbenzene; (iii) reduction of di-nitro-methoxy-pentadecylbenzene to di-amino-methoxy-pentadecylbenzene; and (iv) phosgenation of di-amino-methoxy-pentadecylbenzene to diisocyanato-methoxy-pentadecylbenzene.

A process for the preparation of the biobased diisocyanate of formula 1, may comprise the steps of: (i) nitration of 3-n-pentadecylphenol to di-nitro-pentadecyl-phenol; (ii) acetylation of di-nitro-pentadecyl-phenol to dinitro-5-pentadecylphenyl acetate; (iii) reduction of dinitro-5-pentadecylphenyl acetate to diamino-5-pentadecylphenyl acetate; and (iv) phosgenation of diamino-5-pentadecylphenyl acetate to diisocyanato-diamino-5-pentadecylphenyl acetate.

A process for the preparation of the biobased diisocyanate of formula 1, may comprise the steps of: (i) acetylation of 3-n-pentadecylphenol to 3-pentadecylphenyl acetate; (ii) nitration of 3-pentadecylphenyl acetate to dinitro-5-pentadecylphenyl acetate; (iii) reduction of dinitro-5-pentadecylphenyl acetate to diamino-5-pentadecylphenyl acetate; and (iv) phosgenation of diamino-5-pentadecylphenyl acetate to diisocyanato-diamino-5-pentadecylphenyl acetate.

A process for the preparation of the biobased diisocyanate of formula 2, may comprise the steps of: (i) nitration of 3-n-pentadecylphenol to nitro-pentadecyl-phenol; (ii) etherification of dihaloalkane with nitro-pentadecyl-phenol to bis-(nitro-pentadecyl-phenoxy)-alkane; (iii) reduction of bis-(nitro-pentadecyl-phenoxy)-alkane to bis-(amino-pentadecyl-phenoxy)-alkane; and (iv) phosgenation of bis-(amino-pentadecyl-phenoxy)-alkane to 1,2-bis(isocyanato-pentadecylphenoxy) alkane.

A process for the preparation of the biobased diisocyanate of formula 2, may comprise the steps of: (i) etherification of dihaloalkane with pentadecyl-phenol to bis-(pentadecyl-phenoxy)-alkane; (ii) nitration of bis-(pentadecyl-phenoxy)-alkane to bis-(nitro-pentadecyl-phenoxy)-alkane; (iii) reduction of bis-(nitro-pentadecyl-phenoxy)-alkane to bis-(amino-pentadecyl-phenoxy)-alkane; and iv) phosgenation of bis-(amino-pentadecyl-phenoxy)-alkane to 1,2-bis(isocyanato-pentadecylphenoxy) alkane.

The dihaloalkane may be selected from the group consisting of: 1,2-dichloroethane, 1,2-dibromoethane, 1,2-diiodoethane, 1,3-dichloropropane, 1,3-dibromopropane, 1,4-dichlorobutane, 1,4-dibromobutane, 1,5-dichloropentane, 1,5-dibromopentane, 1,6-dibromohexane, 1,8-dibromooctane, 1,9-dibromononane, 1,10-dibromodecane, 1,12-dibromododecane, 1,18-dibromooctadecane, and mixtures thereof.

In one embodiment, there is provided a polyurethane elastomer derived from: the biobased diisocyanate; and a polyester resin. The polyester resin may be a biobased polyester resin.

BRIEF DESCRIPTION OF THE DRAWINGS

Embodiments will now be described more fully with reference to the accompanying drawings in which.

DETAILED DESCRIPTION OF THE INVENTION

The biobased diisocyanates 1 and 2 (FIG. 1) of the present invention may each be prepared utilizing four distinct process step starting from 3-pentadecyl phenol (Hydrogenated Cardanol), whereby three of the steps are common to established procedures in the art of preparing traditional fossil fuel aromatic based diisocyanates such as toluene diisocyanate (TDI) or 4,4'-methylene diphenyl diisocyanate (MDI). The three steps common to established procedures in the art are nitration, reduction (hydrogenation) and phosgenation. In the present invention, an additional process step is performed to either protect the phenolic OH group of 3-pentadecyl phenol by either a methylation or an acetylation process, or by etherification with a dihaloalkane to result in the bis (phenoxy) alkane derivative. This additional process step can be done directly on the 3-pentadecyl phenol, or with the mono-nitro or dinitro-pentadecyl phenol resulting from the nitration process.

Figure 1:
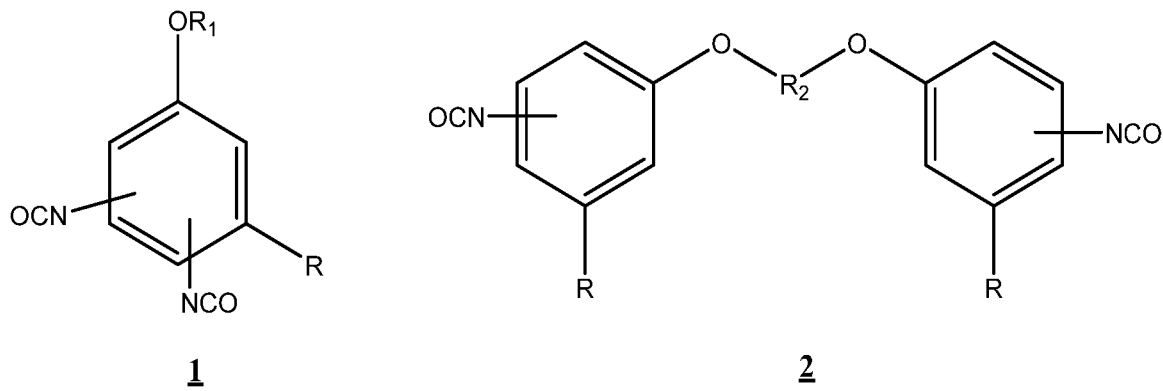
FIG. 1 is a structural view of biobased diisocyanates.
Figure 2:
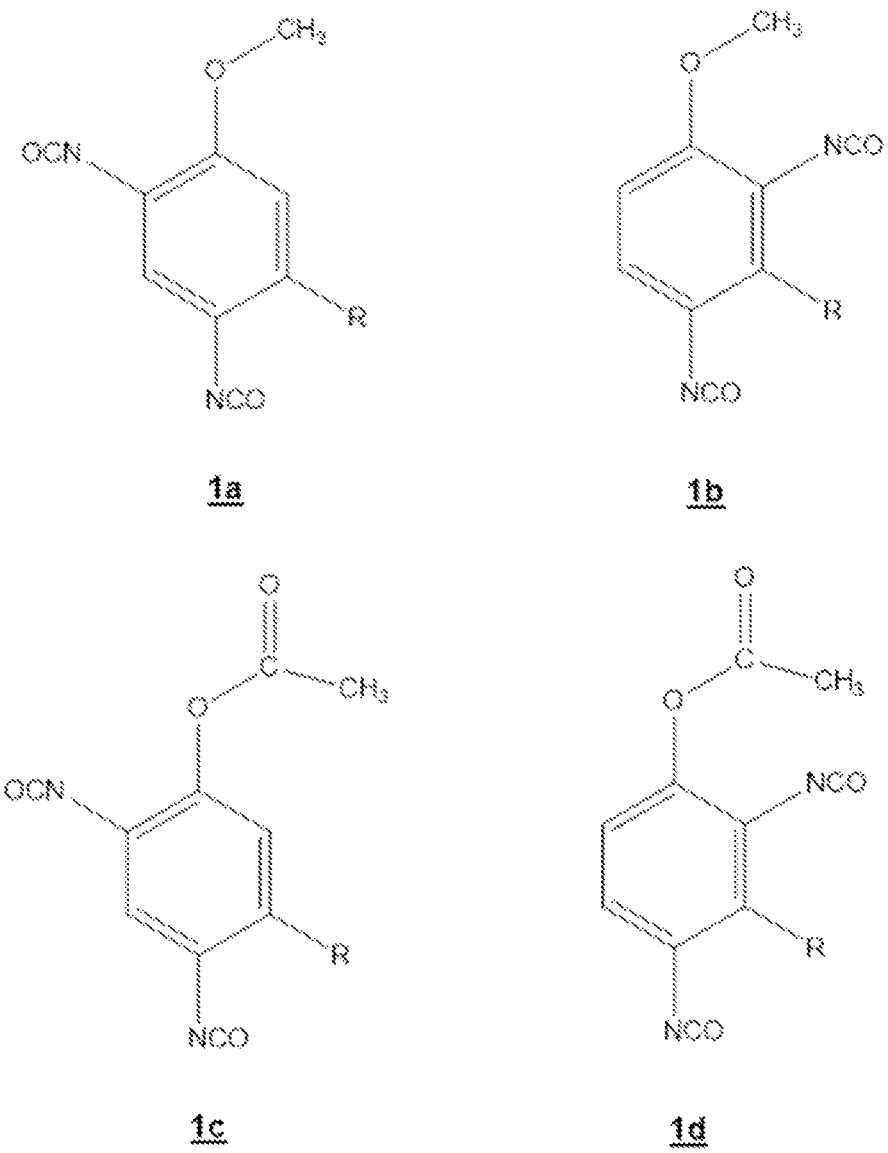
FIG. 2 is a structural view of exemplary embodiments of the biobased diisocyanate 1 shown in FIG. 1.

FIG. 2 shows exemplary embodiments of the biobased diisocyanate 1 illustrated in FIG. 1. These can be defined as 1,5-diisocyanato-2-methoxy-4-pentadecylbenzene (1a), 1,3-diisocyanato-2-methoxy-4-pentadecylbenzene (1b), 2,4-diisocyanato-5-pentadecylphenyl acetate (1c) and 2,6-diisocyanato-3-pentadecylphenyl acetate (1d). Mixtures thereof are contemplated.

Figure 3:
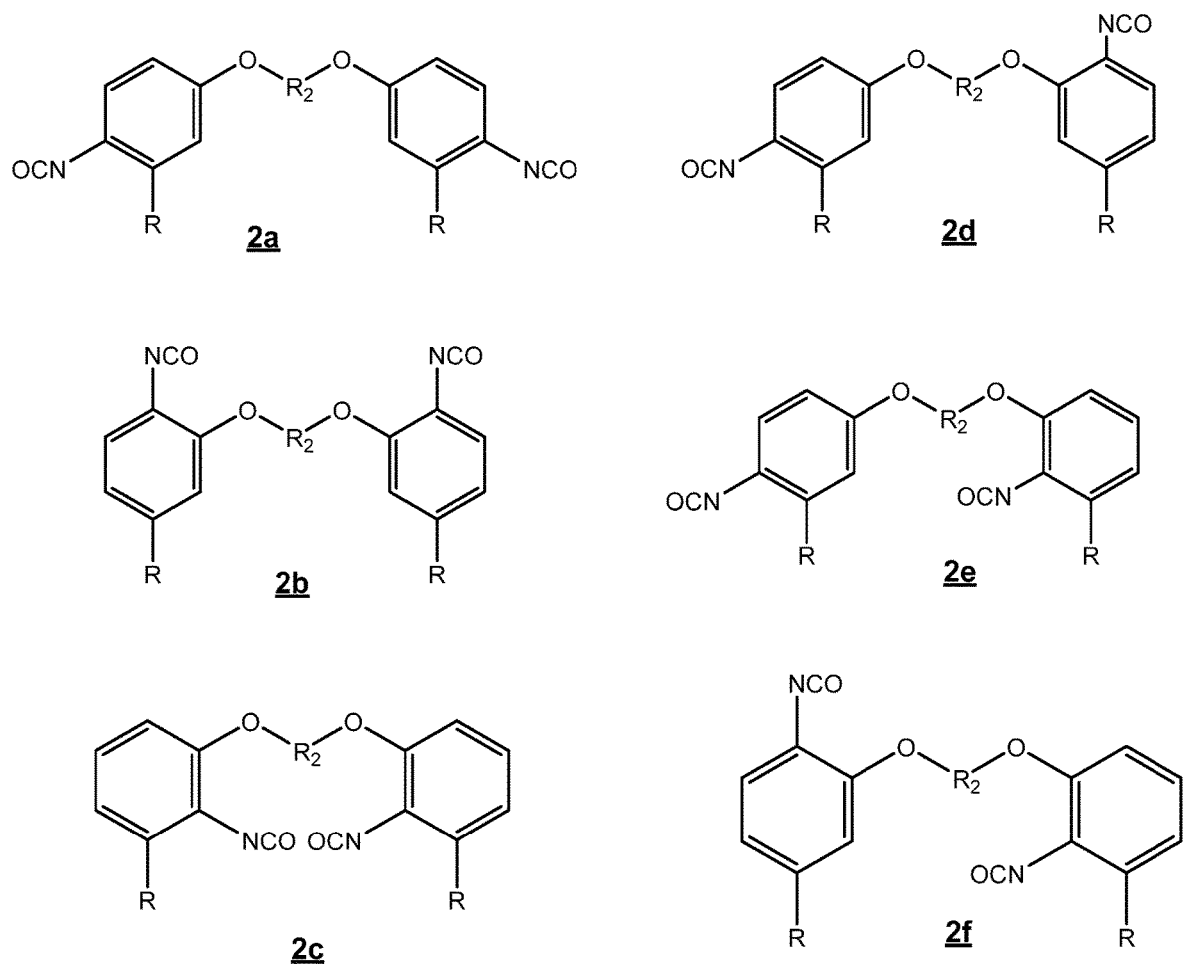
FIG. 3 is a structural view of exemplary embodiments of the biobased diisocyanate 2 shown in FIG. 1.

FIG. 3 shows exemplary embodiments of the biobased diisocyanate 2 illustrated in FIG. 1. These can be defined as 1,2-bis(4-isocyanato-3-pentadecylphenoxy) alkane (2a), 1,2-bis(2-isocyanato-5-pentadecylphenoxy) alkane (2b), 1,2-bis(2-isocyanato-3-pentadecylphenoxy) alkane (2c), 1-isocyanato-2-(2-(4-isocyanato-3-pentadecylphenoxy) alkoxy)-4-pentadecylbenzene (2d), 2-isocyanato-1-(2-(4-isocyanato-3-pentadecylphenoxy) alkoxy)-3-pentadecylbenzene (2e), 2-isocyanato-1-(2-(2-isocyanato-5-pentadecylphenoxy) alkoxy)-3-pentadecylbenzene (2f). Mixtures thereof are contemplated.

Figure 4:
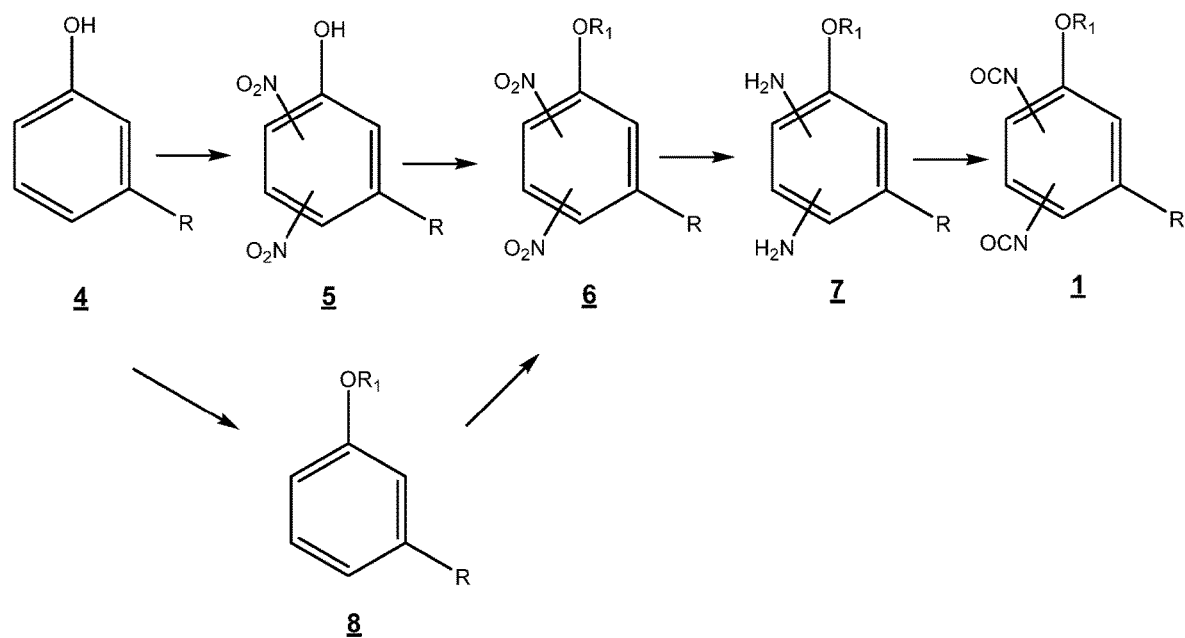
FIG. 4 is a view of process steps used for synthesis of the biobased diisocyanate 1 shown in FIG. 1, wherein $R_1$ is a methyl or acetyl moiety.
Figure 5:
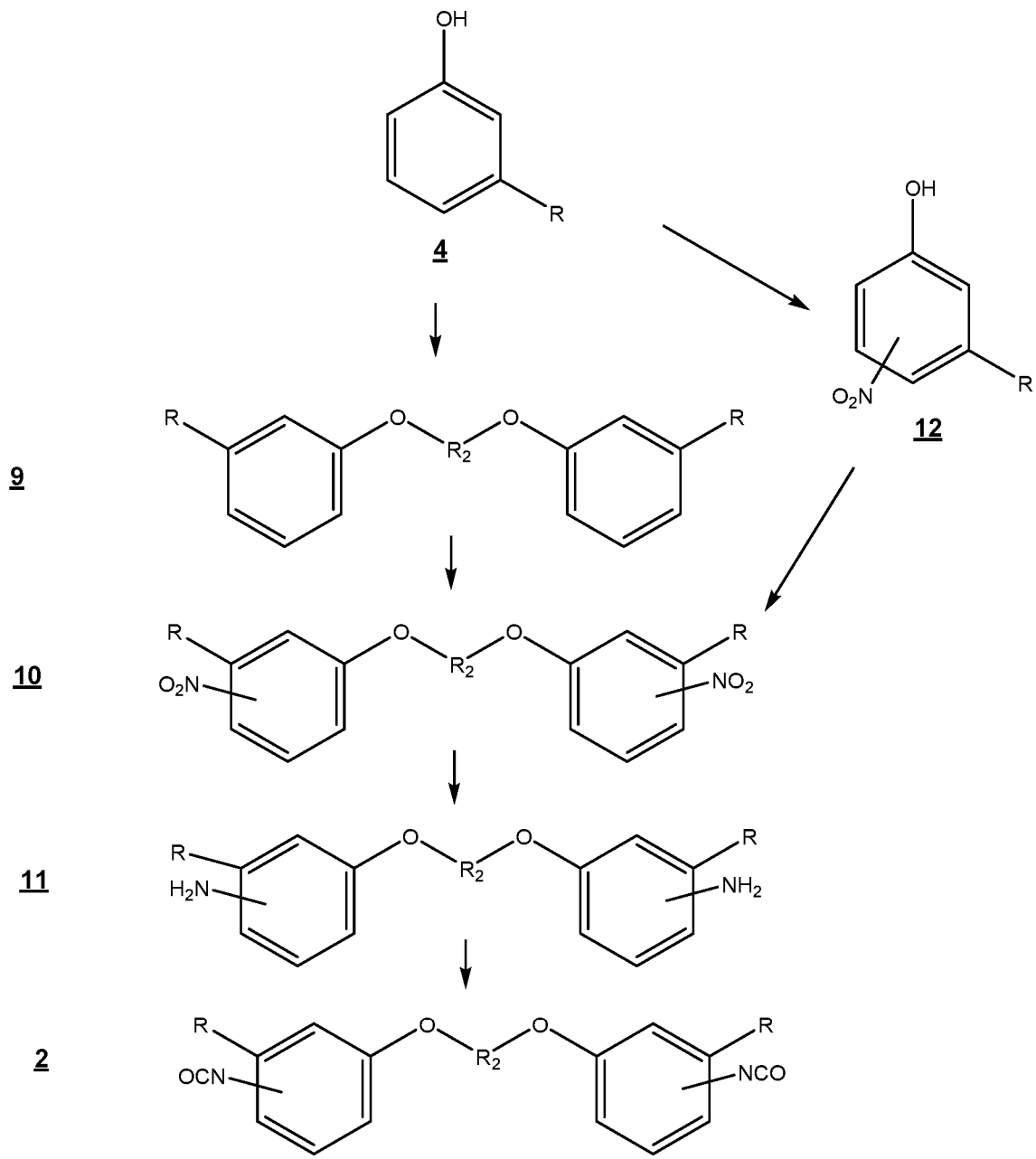
FIG. 5 is a view of process steps used for synthesis of the biobased diisocyanate 2 shown in FIG. 1, wherein $R^2$ is an alkylene.

The preferred process for the preparation of the biobased diisocyanates 1 illustrated in FIG. 1, is shown in FIG. 4 and comprises the steps of: (i) di-nitration of the 3-pentadecylphenol (4) to the corresponding di-nitro-pentadecylphenol (5); (ii) methylation or acetylation to the corresponding di-nitro-methoxy-pentadecylbenzene or di-nitro-pentadecylphenyl-acetate (6); (iii) hydrogenation to the di-amino methoxy-pentadecylbenzene or di-amino-pentadecylphenyl-acetate (7); followed by phosgenation to yield the biobased diisocyanates (1) as illustrated in FIG. 5. Alternatively, the process may comprise the steps of: (i) methylation or acetylation of 3-pentadecylphenol (4) to the corresponding 3-pentadecyl methoxy benzene or 3-pendadecyl-phenyl-acetate (8); (ii) di-nitration to the corresponding di-nitro-methoxy-pentadecylbenzene or di-nitro-pentadecylphenyl-acetate (6); (iii) hydrogenation to the di-amino methoxy-pentadecylbenzene or di-amino-pentadecylphenyl-acetate (7); followed by phosgenation to yield the biobased diisocyanates (1).

The preferred process for the preparation of the biobased diisocyanates 2 illustrated in FIG. 1, wherein $R_2$ is an alkylene from about 1 to 18 carbon atoms, is shown in FIG. 5 and comprises the steps of: (i) mononitration of 3-pentadecylphenol (4) to the corresponding nitro-3-pentadecylphenol (12); (ii) etherification with dihaloalkane to the corresponding bis-(nitro-pentadecyl-phenoxy)-alkane (10); (iii) hydrogenation to the corresponding bis-(amino-pentadecyl-phenoxy)-alkane (11); followed by phosgenation to the corresponding biobased diisocyanates (2), as illustrated in the process steps of FIG. 6. Alternatively, the process may comprise the steps of: (i) etherification with dihaloalkane of 3-pentadecylphenol (4) to the corresponding bis (3-pentadecyl-phenoxy) alkane (9); (ii) mono-nitration to the corresponding bis-(nitro-pentadecyl-phenoxy)-alkane (10); (iii) hydrogenation to the corresponding bis-(amino-pentadecyl-phenoxy)-alkane (11); followed by phosgenation to the corresponding biobased diisocyanates (2).

Nitration

The mono-nitration process step of 3-pentadecylphenol (4), to the corresponding nitro-pentadecylphenol 12, or the di-nitration of (4) to the di-nitro-pentadecyl phenol (5), can be achieved utilizing nitric acid in a solvent such as alcohol, or acetonitrile at room temperature as described by Attanasi et al., "Synthesis and reactions of nitro derivatives of hydrogenated cardanol", Tetrahedron 62, p. 6113 (2006). This procedure can also be utilized in the preparation of the nitration products 6 from 8, or 9 to 10. Other suitable organic solvents for these transformations such as dichloromethane, ether, tetrahydrofuran, can be utilized by those skilled in the art. The nitric acid can be utilized in concentration of 50% to about 90% or by utilizing fumic nitric acid. Acetic acid, acetic anhydride and sulfuric acid can also be utilized in combination with the nitric acid. The various nitration products can be isolated by aqueous (basic) extraction of the residual acid followed by solvent evaporation, and optionally recrystallization of the products. Other known methods of nitration of aromatic compounds are known, such as the solventless process described by Hajipour and Ruoho, "A Fast and Mild Method for Nitration of Aromatic Ring", Phosphorus, Sulfur, and Silicon, 179, p. 221-226 (2004), wherein benzyltriphenylphosphonium nitrate and methanesulfonic acid are utilized with aromatic phenols and anisoles to obtain high yields of nitrated aromatic compounds without the use of solvents. Other known methods of nitration practiced industrially for the production of di-nitrotoluene utilized for the production of TDI can be used, such as those disclosed in U.S. Pat. No. 9,428,441, and in prior art documents cited therein.

Reduction (Hydrogenation)

The reduction of the di-nitro aromatic compounds 6 and 10, to the di-amino aromatic compounds 7, and 11 respectively, can be preferably accomplished by hydrogenation with a catalyst with hydrogen under pressure, as described in U.S. Pat. Nos. 3,328,465, 3,356,728 and 3,517,063, wherein the aromatic dinitro compound is dissolved in a solvent such as methanol and a catalyst such as Raney nickel is employed, at a temperature of from about 100° C. to about 150° C. with a hydrogen pressure of from about 50 atmosphere to about 250 atmosphere. Other catalysts such as platinum, palladium or a combination of platinum and palladium deposited on a carbon support which may be porous or non-porous, can also be utilized. Other methods of reduction of nitro aromatics to amino aromatics are known, such as chemo selective mild reduction described by Kumar et al., "Simple and chemoselective reduction of aromatic nitro compounds to aromatic amines: reduction with hydriodic acid revisited", Tetrahedron Letters 42, p. 5601 (2001), wherein hydroiodic acid is utilized at about 90° C. for 2 to 4 hours to reduce the nitro aromatic compounds to amino aromatic compounds in high yield. Additional methods such as those described by Lauwiner et al., Applied Catalysis A: General 177, p. 9 (1999), can be utilized in the reduction of aromatic nitro compounds with hydrazine hydrate in the presence of an iron oxide/hydroxide catalyst. Other catalysts with hydrazine such as ruthenium have also been reported for the reduction of aromatic nitro compounds. The present invention is not limited to the above reduction process, and a variety of processes known in the literature can be utilized by those skilled in the art.

Phosgenation

The diamino aromatic compounds 7 and 11 can be transformed into the biobased aromatic diisocyanates 1 and 2, utilizing phosgene gas, and similarly to the production process of toluene diisocyanate as described in U.S. Pat. No. 8,034,972, and in prior art documents cited therein. Other known methods utilizing diphosgene (trichloromethyl chloroformate) or triphosgene also known as bis(trichloromethyl) carbonate, which is in liquid rather than gaseous form, can be utilized for the preparation or aromatic diisocyanates from aromatic diamines. A variety of solvents can be utilized for this process, including aprotic solvents such as alkanes, dichloromethane, ether, tetrahydrofuran, ethyl acetate, acetonitrile, and the like, at a temperature range of from about 0° C. to about 60° C., followed by solvent removal by distillation. The resulting diisocyanate products can be optionally fractionally distilled under reduced pressure, recrystallized or utilized without purification.

Methylation

The methylation process for the preparation of di-nitro-methoxy-pentadecylbenzene ($R_1=CH_3$) (6) from di-nitro-pentadecylphenol (5), or the preparation of 3-pentadecyl methoxy benzene ($R_1=CH_3$) (8) from 3-pentadecylphenol (4) can be accomplished utilizing methyl iodide, methyl sulfate or dimethyl carbonate, as described by Selva and Perosa, "Green chemistry metrics: a comparative evaluation of dimethyl carbonate, methyl iodide, dimethyl sulfate and methanol as methylating agents", Green Chemistry 10, p. 457 (2008).

Acetylation

The acetylation process for the formation of di-nitro-pentadecylphenyl-acetate ($R_1=COCH_3$) (6) from di-nitro-pentadecylphenol (5), or the preparation of 3-pendadecyl-phenyl-acetate ($R_1=COCH_3$) (8) from 3-pentadecylphenol (4) can be prepared utilizing acetic anhydride. Various procedures for the acetylation of phenolic compounds have been reported in the literature, and are accomplished by contacting the aromatic phenolic compound with acetic anhydride in the presence of a catalyst from room temperature to about 140° C. Suitable catalysts include, sulfuric acid, p-toluenesulfonic acid ion exchange resins, tetra-alkylammonium halides, and the AMBERLYST 15 catalyst. The reaction can be conducted without the presence of solvents, or can be conducted with aprotic solvents such as alkanes, dichloromethane, ether, tetrahydrofuran, ethyl acetate, acetonitrile, and the like. The present invention is not limited to the above acetylation process, and a variety of processes known in the literature can be utilized by those skilled in the art such as with the use of acetic acid or acetyl chloride.

Etherification

The preparation of bis (3-pentadecyl-phenoxy) alkane (9) is obtained from the etherification of a dihaloalkane with the 3-pentadecylphenol (4). Similarly, the bis-(nitro-pentadecyl-phenoxy)-alkane (10) is obtained from the etherification of a dihaloalkane with the nitro-3-pentadecyl-phenol (12). The dihaloalkane can be selected from 1,2-dichloroethane, 1,2-dibromoethane, 1,2-diiodoethane, 1,3-dichloropropane, 1,3-dibromopropane, 1,4-dichlorobutane, 1,4-dibromobutane, 1,5-dichloropentane, 1,5-dibromopentane, 1,6-dibromohexane, 1,8-dibromooctane, 1,9-dibromononane, 1,10-dibromodecane, 1,12-dibromododecane, 1,18-dibromooctadecane, mixtures thereof, and the like. The reaction is carried out with a base, such as sodium carbonate, potassium carbonate, sodium hydroxide, potassium hydroxide or lithium hydroxide, and is carried out at a temperature of from about 50° C. to about 130° C., with or without the use of an aprotic solvent such as dimethylformamide.

The present invention also contemplates polyurethane elastomers derived primarily from a two-component reaction or curing of the biobased diisocyanate of formula 1 or 2, and a polyol. Preferably, the polyol is a biobased polyol, and more preferably a biobased polyol. In ideal circumstances, the polyol is in liquid form during the reaction at a temperature from about 25° C. to about 80° C. Polyols derived from ethylene oxide and or propylene oxide are typically liquid and of low viscosity under these conditions, although these polyols are generally derived from fossil fuels. Polyols comprised of polyester resins with hydroxyl terminated end groups may also be used, and in some instances are derived from biomass or biobased materials such as those disclosed in U.S. Pat. No. 10,934,384 to Evoco Ltd., issued Mar. 2, 2021, the content of which is herein incorporated by reference in its entirety. These polyester polyols can be solid or viscous liquids at the temperature range of from about 25° C. to about 80° C., and thus require the use of diluents to render them to liquid states. Since there is a desire to utilize biobased polyester polyols, biobased plasticizers can be utilized as effective diluents to solubilize the polyester polyol to a liquid of low viscosity state and for providing the plasticization of the resulting polyurethane elastomer. Ideally, the amount of plasticizer should be added in a minimal enough quantity to solubilize the polyester polyol, and to provide a desirable level of plasticization of the resulting polyurethane elastomer. Such biobased plasticizers have been described, for example, in co-pending U.S. application Ser. No. 17/176,874 to Evoco Ltd., filed Feb. 16, 2021, the content of which is herein incorporated by reference in its entirety. From about 85 to about 99% of the weight of the polyurethane elastomer may be derived from biobased content.

Specific embodiments of the present disclosure as illustrated in the following Examples are for illustrative purposes and are not limited to the materials, conditions, or process parameters set forth in these embodiments.

Example 1

General Procedure for the Di-Nitration Reactions: Preparation of Di-nitro-pentadecyl-phenol (5).

To a 1 L three necked flask equipped with an overhead stirrer, was added 500 mL of acetonitrile and 304.5 grams of 3-n-pentadecylphenol (4), cooled to about 0° C. to 5° C. with an ice/water bath. To this was added 2 moles of nitric acid (70%) in 100 mL of acetonitrile dropwise over a 30 min period. The mixture was allowed to warm up to room temperature over a 3-hour period, and stirring was maintained for an additional hour. The mixture was then transferred to a 1.5 L separatory funnel, washed with a 1% aqueous solution of sodium carbonate, followed by water and the organic layer was then rotary evaporated to yield a mixture of about 92% di-nitro-pentadecyl-phenol (5). The product was then recrystallized from hexane and characterized by NMR spectroscopy.

Example 2

General Procedure for the Methylation Reactions: Preparation of Di-nitro-methoxy-pentadecylbenzene ($R_1=CH^3$) (6).

To a 300 mL Parr autoclave reactor equipped with a magnetic stirrer was added 100 grams of the di-nitro-pentadecyl-phenol (5) of Example 1, 60 grams of dimethyl carbonate and 0.5 grams of anhydrous potassium carbonate. The mixture was heated to 150° C. to 160° C. for 12 hours. The reactor was then left to cool overnight to room temperature, and the contents were subjected to vacuum filtration and the resulting solution stripped of residual methanol and dimethyl carbonate by rotary evaporation to yield 94 grams of the di-nitro-methoxy-pentadecylbenzene (6).

Example 3

General Procedure for the Reduction Reactions: Preparation of Di-amino-methoxy-pentadecylbenzene ($R_1=CH_3$) (7).

To a 250 mL 3 necked flask equipped with a magnetic stirrer and reflux condenser was added 25 grams of the di-nitro-methoxy-pentadecylbenzene (6) of Example 2, 150 mL of ethanol, 3.2 grams hydrazine monohydrate and 0.25 grams of iron oxide/hydroxide catalyst. The mixture was heated to 75° C. for 3 hours and then allowed to cool to room temperature. The mixture was then vacuum filtered and the ethanol was removed by rotary evaporation to yield 19 grams of the di-amino-methoxy-pentadecylbenzene (7).

Example 4

General Procedure for the Triphosgenation Reactions: Preparation of Diisocyanato-methoxy-pentadecylbenzene ($R_1$=$CH^3$) (1).

To a 250 mL 3 necked flask equipped with a magnetic stirrer and reflux condenser was added 100 mL of ethyl acetate, 15 grams of the di-amino-methoxy-pentadecylbenzene (7) of Example 3, and a solution of triphosgene (12 g) in 50 mL of ethyl acetate over a period of 20 minutes. The mixture was then refluxed under nitrogen for 4 h. After allowing the reaction to cool to room temperature, the solvent was evaporated under reduced pressure and the residue obtained was subjected to distillation in a Kugelrohr apparatus, to yield 15.5 grams of the diisocyanato-methoxy-pentadecylbenzene (1). The diisocyanate of this example was calculated to be 75.3% biobased, by weight.

Example 5

General Procedure for the Mono-Nitration Reactions: Preparation of Nitro-pentadecylphenol (12).

To a 1 L three necked flask equipped with an overhead stirrer, was added 500 mL of acetonitrile, 304.5 grams of 3-n-pentadecylphenol (4) and cooled to about 0° C. to 5° C. with an ice/water bath. To this was added 1 mole of nitric acid (70%) in 100 mL of acetonitrile dropwise over a 30 min period. The mixture was allowed to warm up to room temperature over a 3-hour period, and stirring was maintained for an additional hour. The mixture was then transferred to a 1.5 L separatory funnel, washed with a 1% aqueous solution of sodium carbonate, followed by water, and the organic layer was then rotary evaporated to yield a mixture of about 91% of the nitro-pentadecyl-phenol (12). The product was characterized by NMR spectroscopy.

Example 6

General Procedure for the Etherification Reactions: Preparation of Bis-(nitro-pentadecyl-phenoxy)-ethane ($R_2$=$CH_2CH_2$) (10).

To a 500 mL 3 necked flask equipped with a magnetic stirrer and a reflux condenser was added 50 grams of the nitro-3-pentadecyl-phenol (12) of Example 5, 45 grams of anhydrous potassium carbonate and 250 mL of N, N-dimethylformamide. The reaction mixture was heated at 110° C. for 1 h and then 13.6 grams of 1,2-dibromoethane were added dropwise. The heating was then continued at 110° C. for an additional hour. The reaction mixture was poured into ice cold water (500 mL), and the product was collected by filtration, dissolved in 200 mL of dichloromethane and washed with water, and the solvent was rotary evaporated to obtain 22 grams of the bis-(nitro-pentadecyl-phenoxy)-ethane (10).

Example 7

Preparation of Bis-(amino-pentadecyl-phenoxy)-ethane ($R^2$=$CH^2CH^2$) (11).

To a 250 mL 3 necked flask equipped with a magnetic stirrer and reflux condenser was added 20 grams of the bis-(nitro-pentadecyl-phenoxy)-ethane (10) of Example 6, 150 mL of ethanol, 1.6 grams of hydrazine monohydrate and 0.2 grams of iron oxide/hydroxide catalyst. The mixture was heated to 75° C. for 3 hours and then allowed to cool to room temperature. The mixture was then vacuum filtered, and the ethanol was removed by rotary evaporation to yield 15 grams of the bis-(amino-pentadecyl-phenoxy)-ethane (11).

Example 8

Preparation of 1,2-bis(isocyanato-pentadecylphenoxy) Ethane ($R_2$=$CH_2CH_2$) (2).

To a 250 mL 3 necked flask equipped with a magnetic stirrer and reflux condenser was added 100 mL of ethyl acetate, 15 grams of the bis-(amino-pentadecyl-phenoxy)-ethane (11) of Example 7, and a solution of triphosgene (6 g) in 50 mL of ethyl acetate over a period of 20 minutes. The mixture was then refluxed under nitrogen for 4 h. After allowing the reaction to cool to room temperature, the solvent was evaporated under reduced pressure and the residue obtained was subjected to distillation in a Kugelrohr apparatus, to yield 15.1 grams of the 1,2-bis(isocyanato-pentadecylphenoxy) ethane ($R_2$=$CH_2CH_2$) (2). The diisocyanate of this example was calculated to be 84.4% biobased, by weight.

What is claimed is:

1. A biobased diisocyanate of the formula 1 or 2:

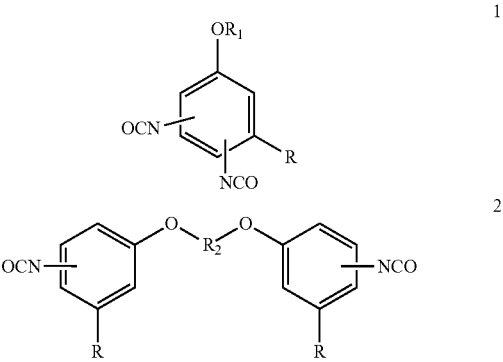

wherein R is an alkyl chain $C_{15}H_{31}$; $R_1$=$COCH_3$; and $R_2$ is an alkylene of from about 1 to 18 carbon atoms.

2. The biobased diisocyanate of claim 1, wherein formula 1 is selected from the group consisting of: 2,4-diisocyanato-5-pentadecylphenyl acetate, and 2,6-diisocyanato-3-pentadecylphenyl acetate, and mixtures thereof.

3. The biobased diisocyanate of claim 1, wherein formula 2 is selected from the group consisting of: 1,2-bis(4-isocyanato-3-pentadecylphenoxy) ethane, 1,2-bis(2-isocyanato-5-pentadecylphenoxy) alkane, 1,2-bis(2-isocyanato-3-pentadecylphenoxy) alkane, 1-isocyanato-2-(2-(4-isocyanato-3-pentadecylphenoxy) alkoxy)-4-pentadecylbenzene, 2-isocyanato-1-(2-(4-isocyanato-3-pentadecylphenoxy) alkoxy)-3-pentadecylbenzene, 2-isocyanato-1-(2-(2-isocyanato-5-pentadecylphenoxy) alkoxy)-3-pentadecylbenzene, and mixtures thereof.

4. The biobased diisocyanate of claim 1, wherein the diisocyanate is from about 70 to about 85% biobased, by total weight of the diisocyanate.

5. A process for the preparation of the biobased diisocyanate of claim 1, formula 1, comprising the steps of: (i) nitration of 3-n-pentadecylphenol to di-nitro-pentadecyl-phenol; (ii) acetylation of di-nitro-pentadecyl-phenol to dinitro-5-pentadecylphenyl acetate; (iii) reduction of dinitro-5-pentadecylphenyl acetate to diamino-5-pentadecylphenyl acetate; and (iv) phosgenation of diamino-5-pentadecylphenyl acetate to diisocyanato-diamino-5-pentadecylphenyl acetate.

6. A process for the preparation of the biobased diisocyanate of claim 1, formula 1, comprising the steps of: (i) acetylation of 3-n-pentadecylphenol to 3-pentadecylphenyl acetate; (ii) nitration of 3-pentadecylphenyl acetate to dinitro-5-pentadecylphenyl acetate; (iii) reduction of dinitro-5-pentadecylphenyl acetate to diamino-5-pentadecylphenyl acetate; and (iv) phosgenation of diamino-5-pentadecylphenyl acetate to diisocyanato-diamino-5-pentadecylphenyl acetate.

7. A process for the preparation of the biobased diisocyanate of claim 1, formula 2, comprising the steps of: (i) nitration of 3-n-pentadecylphenol to nitro-pentadecyl-phenol; (ii) etherification of dihaloalkane with nitro-pentadecyl-phenol to bis-(nitro-pentadecyl-phenoxy)-alkane; (iii) reduction of bis-(nitro-pentadecyl-phenoxy)-alkane to bis-(amino-pentadecyl-phenoxy)-alkane; and (iv) phosgenation of bis-(amino-pentadecyl-phenoxy)-alkane to 1,2-bis(isocyanato-pentadecylphenoxy) alkane.

8. The process of claim 7, wherein the dihaloalkane is selected from the group consisting of: 1,2-dichloroethane, 1,2-dibromoethane, 1,2-diiodoethane, 1,3-dichloropropane, 1,3-dibromopropane, 1,4-dichlorobutane, 1,4-dibromobutane, 1,5-dichloropentane, 1,5-dibromopentane, 1,6-dibromohexane, 1,8-dibromooctane, 1,9-dibromononane, 1,10-dibromodecane, 1,12-dibromododecane, 1,18-dibromooctadecane, and mixtures thereof.

9. A process for the preparation of the biobased diisocyanate of claim 1, formula 2, comprising the steps of: (i) etherification of dihaloalkane with pentadecyl-phenol to bis-(pentadecyl-phenoxy)-alkane; (ii) nitration of bis-(pentadecyl-phenoxy)-alkane to bis-(nitro-pentadecyl-phenoxy)-alkane; (iii) reduction of bis-(nitro-pentadecyl-phenoxy)-alkane to bis-(amino-pentadecyl-phenoxy)-alkane; and iv) phosgenation of bis-(amino-pentadecyl-phenoxy)-alkane to 1,2-bis(isocyanato-pentadecylphenoxy) alkane.

10. The process of claim 9, wherein the dihaloalkane is selected from the group consisting of: 1,2-dichloroethane, 1,2-dibromoethane, 1,2-diiodoethane, 1,3-dichloropropane, 1,3-dibromopropane, 1,4-dichlorobutane, 1,4-dibromobutane, 1,5-dichloropentane, 1,5-dibromopentane, 1,6-dibromohexane, 1,8-dibromooctane, 1,9-dibromononane, 1,10-dibromodecane, 1,12-dibromododecane, 1,18-dibromooctadecane, and mixtures thereof.

11. A polyurethane elastomer derived from:
the biobased diisocyanate of claim 1; and
a polyester resin.

12. The polyurethane of claim 11, wherein the biobased diisocyanate is the biobased diisocyanate of formula 1, and is selected from the group consisting of: 2,4-diisocyanato-5-pentadecylphenyl acetate, and 2,6-diisocyanato-3-pentadecylphenyl acetate, and mixtures thereof.

13. The polyurethane of claim 11, wherein the biobased diisocyanate is the biobased diisocyanate of formula 2, and is selected from the group consisting of: 1,2-bis(4-isocyanato-3-pentadecylphenoxy) ethane, 1,2-bis(2-isocyanato-5-pentadecylphenoxy) alkane, 1,2-bis(2-isocyanato-3-pentadecylphenoxy) alkane, 1-isocyanato-2-(2-(4-isocyanato-3-pentadecylphenoxy) alkoxy)-4-pentadecylbenzene, 2-isocyanato-1-(2-(4-isocyanato-3-pentadecylphenoxy) alkoxy)-3-pentadecylbenzene, 2-isocyanato-1-(2-(2-isocyanato-5-pentadecylphenoxy) alkoxy)-3-pentadecylbenzene, and mixtures thereof.

14. The polyurethane of claim 11, wherein the polyester resin is a biobased polyester resin.

15. The polyurethane of claim 11, wherein from about 85 to about 99% of the weight of the polyurethane elastomer is derived from biobased content.

\* \* \* \* \*